United States Patent [19]

Davis et al.

[11] Patent Number: 4,910,021

[45] Date of Patent: Mar. 20, 1990

[54] TARGETED ENTERNAL DELIVERY SYSTEM

[75] Inventors: John D. Davis, Grossepointe Farms, Mich.; Elka Touitou; Ardon Rubinstein, both of Jerusalem, Israel

[73] Assignee: R. P. Scherer Corporation, Troy, Mich.

[21] Appl. No.: 934,741

[22] Filed: Nov. 25, 1986

[30] Foreign Application Priority Data

Nov. 29, 1985 [IT] Italy .................................. 77186

[51] Int. Cl.$^4$ ............................................ A11K 9/64
[52] U.S. Cl. ................................. 424/456; 424/463; 424/45
[58] Field of Search ............... 424/463, 462, 480, 482, 424/494, 497, 456, 457

[56] References Cited

U.S. PATENT DOCUMENTS

| | | | |
|---|---|---|---|
| 3,656,997 | 4/1972 | Cordes | 424/81 |
| 4,022,889 | 5/1977 | Bannister et al. | 514/43 |
| 4,031,215 | 6/1977 | Sasaki et al. | 514/183 |
| 4,042,688 | 8/1977 | Gans et al. | 514/801 |
| 4,406,896 | 9/1983 | Higuchi et al. | 424/232 |
| 4,433,966 | 2/1984 | Zeltoun et al. | 424/21 |
| 4,434,159 | 2/1984 | Sekine et al. | 424/178 |
| 4,464,363 | 8/1984 | Higuchi et al. | 424/232 |
| 4,525,339 | 6/1985 | Behl et al. | 42/459 |
| 4,675,189 | 6/1987 | Kint et al. | 424/490 |

FOREIGN PATENT DOCUMENTS

| | | | |
|---|---|---|---|
| 0036534 | 7/1980 | European Pat. Off. | 31/62 |
| 0036145 | 9/1981 | European Pat. Off. | 31/62 |
| 0108295 | 10/1982 | European Pat. Off. | 31/43 |
| 1159236 | 3/1968 | United Kingdom | 13/2 |
| 2123695 | 2/1984 | United Kingdom | . |

OTHER PUBLICATIONS

Touitou et al., J. Pharm. Pharnacol., (1980), 32, 108–110.

Rubinstein et al., Antimicrol Agents and Chemotherapy (1980) 19 (5) 696–699.

Primary Examiner—Ellis P. Robinson
Assistant Examiner—Len E. Horne
Attorney, Agent, or Firm—Allegretti & Witcoff, Ltd.

[57] ABSTRACT

A capsule for oral administration of a pharmaceutically active ingredient contains a pharmaceutical composition comprising the active ingredient, for example, a peptide, an absorption promoter and usually, a carrier. The absorption promoter is capable of enhancing absorption of the active ingredient from the intestine into the bloodstream. The capsule is coated with a film forming composition, which film is sufficiently insoluble at a pH below 7 as to be capable of protecting the capsule and its contents from the digestive juices until the capsule reaches a region below the upper part of the intestine, whereupon the coating and capsule are capable of eroding or dissolving to release the active ingredient for absorption into the bloodstream.

12 Claims, 4 Drawing Sheets

TARGETED ENTERNAL DELIVERY SYSTEM

This invention relates to a targeted enteral delivery system which enables a medicament to be released at a region of the intestine such as the colon at which the medicament is not significantly adversely affected by digestive juices.

Certain drugs such as insulin and other proteins or peptides if administered orally to a patient and allowed to pass unprotected through the stomach, exhibit poor efficacy.

For example, the poor efficacy of orally administered insulin in diabetic patients is mainly due to two properties of this substance:

(a) insulin is a pancreatic hormone peptide and thus subject to proteolytic inactivation during the passage through the gastro-intestinal tract, mainly in its upper region;

(b) insulin has a high tendency for self-association to form high molecular weight oligomers and as a result of this increase in molecular weight the amount of insulin passing through enteral membranes by diffusion is not sufficient to achieve appreciable therapeutic effects.

It has been shown by coinventors of the present invention (Touitou et al., J. Pharm. Pharmacol. (1980), 32, 108-110) that significant hypoglycemia can be induced in rats when insulin is injected intrajejunally in the presence of a non-ionic surfactant, Cetamacrogol TM 1000, as absorption promoter. They suggested that insulin absorption might be accomplished by oral administration of a suitably designed product containing insulin and surfactant provided that the insulin were protected against degradation by a suitable coating during its passage to the jejunal absorption site.

U.S. Pat. No. 4406896 and U.S. Pat. No. 4464363 describe rectally administered drug forms which include, in addition to the drug, an absorption promoter such as 5-methoxysalicylic acid for enhancing absorption of the drug into the bloodstream from the rectum.

Such rectal administration is, however, inconvenient to the patient.

GB No.-B-2123695 describes orally administrable dosage forms consisting of a tablet or capsule containing 5-amino-salicylic acid for local treatment of colonic or rectal disorders. The dosage form is coated with a 60 to 150 micron thick layer of Eudragit S—a commercially available anionic polymer which is a partly methyl esterified methacrylic acid polymer ("Eudragit" is a trade mark). The coating is insoluble in the gastric and intestinal juices below pH 7 but soluble in colonic juices, so that the oral dosage form remains intact until it reaches the colon.

U.S. patent application No. 4432966 describes compressed tablets for disintegration in the colon, which tablets contain active ingredients such as neomycin and prednisolone. The tablets are provided with a double coating, the inner of which contains microcrystalline cellulose and a film-forming polymer which is not degraded by a neutral or alkaline medium, and the outer of which is a pharmaceutically acceptable enteric coating.

However, such compositions have not been designed to allow significant amounts of active ingredient to be absorbed into the bloodstream.

Thus, although highly desirable from a practical point of view, unit dosage forms for the oral administration of drugs such as insulin which drugs are susceptible to attack by the digestive juices, have not, to date, been successful.

The problem therefore is both to protect drugs such as peptides from proteolysis and to achieve useful absorption from the colon into the bloodstream. We have found a delivery system of a coated capsule with certain substances in the capsule contents which leads to an enhancement of absorption from the intestine.

This delivery system results in a decrease in drug inactivation and an increase in drug absorption.

The invention provides a capsule for oral administration of a pharmaceutically active ingredient (hereinafter "drug") which capsule contains a pharmaceutical composition, which composition comprises the drug, an absorption promoter capable of enhancing absorption of the drug from the intestine into the bloodstream, and, if appropriate, a suitable pharmaceutically acceptable excipient, and which capsule is coated with a film forming composition, which film is sufficiently insoluble at a pH below 7 as to be capable of protecting the capsule and its contents from the digestive juices until the capsule reaches a region in which the active ingredient will not be significantly adversely affected by the digestive juices, whereupon the coating and capsule are capable of eroding or dissolving so as to release the drug for absorption into the bloodstream.

A targeted enteral delivery system in accordance with the invention is especially applicable to any drug which (i) is poorly absorbed, and/or (ii) is degraded by the gastric or smaller-intestinal juices, and/or (iii) induces side effects in the stomach/small intestine, but is particularly useful for administration of therapeutically useful peptide or protein drugs, for example insulin, gastrin, pentagastrin, calcitonin, human growth hormone, glucagon, adrenocorticotrophic hormone, leutinising releasing hormone, enkephalin, oxycotin, parathyroid hormone, thyrotropic releasing hormone and vasopressin.

The capsules are adapted to effectively release the drug at any region within the lower part of the gastrointestinal tract, where proteolysis is rather low. Such release may occur at any region below the upper part of the small intestine, including the lower part of the small intestine, and including the rectum. However, preferred capsules release the drug in the jejunum or colon, especially the colon.

A particularly preferred dosage form is one comprising insulin contained in gelatin capsules coated with a suitable polymer, such as a polyacrylic polymer which has pH dependent properties.

The capsule may be a soft or hard gelatin capsule.

A soft gelatin capsule shell is preferably prepared from a capsule composition comprising gelatin, or a substituted gelatin, e.g. phthallated or succinated gelatin, and a plasticiser such as a polyhydric alcohol, e.g. glycerol. For specific cases, a blend of polyhydric alcohols, or a blend of one or more polyhydric alcohols with other plasticisers is preferred, for example, a blend of glycerol with a sorbitol solution or a blend of glycerol with a sorbitol/sorbitan mixture.

The soft gelatin capsule compositions additionally include water (which is evaporated off on drying) and may additionally include other additives such as opacifiers, e.g. silicone oil, preservatives, e.g. potassium sorbate and colours.

The soft gelatin capsule shell composition (before drying) preferably comprises 30–53 parts gelatin or substituted gelatin, 15–48 parts plasticiser and 16–40 parts water, the parts being by weight of the total weight of the composition.

In the dried capsule, the gelatin or substituted gelatin usually amounts to 40–70% and the plasticiser to 10–50% by weight of the total weight of the composition.

A typical soft gelatin capsule composition (after drying) comprises essentially

| | |
|---|---|
| Gelatin | 57.65% w/w |
| Glycerin | 28.95% w/w |
| Silicone Oil | 13.14% w/w |
| Potassium Sorbate | 0.26% w/w |

A hard gelatin capsule shell is preferably prepared from a capsule composition comprising gelatin and a small amount of plasticiser such as glycerol.

As an alternative to gelatin, the capsule shell may be made of a carbohydrate material.

The capsule composition may additionally include colourings, flavourings and opacifiers as required.

The absorption promoter of a pharmaceutical composition present in a capsule in accordance with the invention is preferably an organic aromatic carboxylic acid or ester or amide thereof. Examples are salicylic acid and salicylates such as 5-methoxysalicylic acid; 5-methylsalicylic acid; 3-methylsalicylic acid; 5-tert-octylsalicylic acid; 3-tert-butyl-6-methylsalicylic acid; 3,5-diisopropylsalicylic acid; 3-tert-butyl-5-methylsalicylic acid; 5-bromosalicylic acid; 3,5-diiodosalicylic acid; 3-methoxysalicylic acid; 5-octyloxysalicylic acid; 5-butoxysalicylic acid; 5-chlorosalicylic acid; and the sodium salts thereof.

Other examples are homovanillic acid; 2,5-dihydroxybenzoic acid; 2,4-dihydroxybenzoic acid; 5-methoxy-2-hydroxyphenylsulfonic acid; guaicolsulfonic acid; 2-hydroxyphenylacetic acid; 2hydroxyphenylmethanesulfonic acid; 5-trifluoro methyl-2-hydroxybenzoic acid; 2-hydroxy-3-methoxybenzoic acid; and the sodium salts thereof.

Other useful absorption promoters are surface active agents such as a mixture of (a) a higher fatty acid salt and (b) a fatty alcohol or glyceride. The glyceride may be a mono- or di-glyceride.

A preferred surface active agent is a mixture of sodium laurate with cetyl alcohol, stearyl alcohol, glyceryl monostearate or glyceryl monocaproate, especially a sodium laurate/cetyl alcohol mixture.

The choice of absorption promoter depends upon the drug and promoters which enhance absorption of peptides or proteins such as insulin, pentagastrin and gastrin with particularly excellent effects are 5-methoxysalicylic acid; salicylic acid; 2,5-dihydroxybenzoic acid; 2,4-dihydroxybenzoic acid; 3-methylsalicylic acid; 5-methylsalicylic acid; 5-tert-octylsalicylic acid; 3-tert-butyl-6-methylsalicylic acid; 3,5-diisopropylsalicylic acid; 3-tert-butyl-5-methylsalicylic acid; 5-bromosalicylic acid; 3,5-dibromosalicylic acid; 5-iodosalicylic acid; 3,5-diiodosalicylic acid; 2-hydroxy-phenylacetic acid; 5-trifluoromethyl-2-hydroxybenzoic acid; 3-methoxysalicylic acid; 5-octyloxysalicylic acid; 5-butoxysalicylic acid; 5-chlorosalicylic acid; 2-hydroxy-3-methoxybenzoic acid; and the sodium salts thereof.

Good absorption of insulin is also achieved using a sodium laurate/cetyl alcohol (1:4) surfactant mixture.

Promoters which enhance the absorption of β-lactam antiobiotic drugs such as penicillin G, ampicillin, amoxicillin, methacillin, carbenicillin, cefoxitin, cephamandole, cephaprin, cephmetazole, cephanone, oxacephalosporin, and N-formimidoyl thienamycin with particularly excellent effects are 5-methoxy-salicylic acid; salicylic acid; homovanillic acid; 2,5-dihydroxybenzoic acid; 2,4-dihydroxybenzoic acid; 5-methoxy-2-hydroxyphenylsulfonic acid; 3-methylsalicylic acid; 5-methylsalicylic acid; 5-tertoctylsalicylic acid; 3-tert-butyl-6-methylsalicylic acid; 3,5-diisopropylsalicylic acid; 3-tert-butyl -5-methylsalicylic acid; guaicolsulfonic acid; 5-bromosalicylic acid; 3,5-dibromosalicylic acid; 5-iodosalicylic acid, 3,5-diiodosalicylic acid; 2-hydroxyphenylacetic acid; 2-hydroxyphenylmethanesulfonic acid; 5-trifluoromethyl-1-hydroxybenzoic acid; 3-methoxysalicylic acid; 5-octyloxysalicylic acid; 5-butoxysalicylic acid; 3,4-dihydroxyphenylacetic acid; 5-chlorosalicylic acid; 2-hydroxy-3-methoxybenzoic acid; salicyluric acid; and the sodium salts thereof.

Generally the amount of absorption promoter in our drug forms is from 1–1000 mg in each unit dose. The percentage of absorption promoter in the total combination of drug plus absorption promoter is usually 20–95% with a preferred ratio of promoter in the total combination of promoter plus drug being 30–60%. A most preferred ratio of promoter to promoter plus drug is 50%.

In addition to the drug and absorption promoter, the pharmaceutical composition usually includes a carrier such as polyethylene glycol having a molecular weight of from 400–5000, preferably from 600–4000, and more preferably a mixture of a solid polyethylene glycol having a molecular weight of, say, 4000 and a liquid polyethylene glycol having a molecular weight of, say, 600, or an oil, for example; soya bean oil, arachis oil, or an ester of a medium chain fatty acid, for example a triglyceride of fractionated coconut oil $C_{8-10}$ fatty acids, e.g. a caprylic/capric triglyceride mixture optionally including a small amount, say 5%, linoleic acid, or a propylene glycol diester of saturated $C_{8-10}$ fatty acids e.g. a propylene dicaprylate/dicaprate mixture.

The coating composition is preferably an anionic copolymer of methacrylic acid and a methacrylic acid ester, such copolymers being commercially available under the trade name "Eudragit"(TM). Eudragit may be used in a variety of forms. Such a copolymer, or more preferably a mixture of such copolymers, may also be admixed with a further film-forming component such as ethyl cellulose (available under the trade name "Ethocel") or shellac.

Typical methacrylic acid/methacrylate copolymers are:

Eudragit RS—a copolymer derived from acrylic and methacrylic acid esters with a low content of quaternary ammonium groups. The molar ratio of these ammonium groups to the remaining neutral (meth)acrylic acid esters is 1:40. The mean molecular weight of the copolymer is approximately 150,000.

Eudragit S—an anionic copolymer derived from methacrylic acid and methyl methacrylate. The ratio of free carboxyl groups to the esters is approximately 1:2. The mean molecular weight of the copolymer is approximately 135,000.

Eudragit L—an anionic copolymer derived from methacrylic acid and methyl methacrylate. The ratio of free carboxyl groups to the ester groups is approximately 1:1. The mean molecular weight of the copolymer is approximately 135,000.

Various forms of Eudragit were examined for various delivery systems and amongst satisfactory systems there may be mentioned soft gelatin capsules filled with a quantity of the order of 100 mg containing 8 iu porcine insulin, 20 mg of surfactant mixture (sodium laurate: cetyl alcohol 1:4) in arachis oil. The capsules were coated with various mixtures of Eudragit RS, L and S.

The in-vitro pH dependent release rates of coated capsules were tested by scintillation counting using $^{125}$I-insulin. Two dosage forms including respective coating compositions which gave best results as regards release at a pH in the 7.5 to 8.0 range (RS1 and RS2) were chosen for further studies with rats. Such capsules were administered to male rats (270 g) and insulin absorption was measured by the determination of the resulting hypoglycemia effect. The oral administration of the two dosage forms of choice gave a significant (p 0.01) hypoglycemia when compared with controls. Duration, course and intensity of effect were different for each of the tested formulations, as will be shown in detail hereinafter. The pre-administration of a capsule containing a surfactant did not change the glycemic profile; the post-administration prolonged the effect of RS2 from 1 to 2 hours.

Embodiments of the invention will now be described in more detail with reference to the following Examples and accompanying drawings which are explained later in a legend.

EXAMPLES OF PHARMACEUTICAL COMPOSITIONS FOR INSERTION INTO GELATIN CAPSULES

EXAMPLES 1-3

Three formulations, based on polyethylene glycol and containing the peptide drugs insulin, calcitonin and human growth hormone respectively, for encapsulation in capsules embodying the invention are as follows.

| Ingredient | Example 1 Insulin | Example 2 Calcitonin (Pork) | Example 3 Human Growth Hormone |
|---|---|---|---|
| Peptide | 20 i.u. (ca. 1 mg) | 80 i.u. (ca. 1 mg) | 4 i.u. (ca. 2 mg) |
| Sodium 5-methoxy salicylate (1) | 150.0 mg | 150.0 mg | 150.0 mg |
| PEG 4000 (2) | 3.5 mg | 3.5 mg | 3.5 mg |
| PEG 600 (3) | 187.5 mg | 187.5 mg | 186.5 mg |
| Capsule fill wt | 342 mg | 342 mg | 342 mg |

(1) absorption promoter
(2) polyethylene glycol having a molecular weight of 4000 - a solid thickener which increases viscosity and allows suspension of solid particles.
(3) polyethylene glycol having a molecular weight of 600 - a liquid suspending agent.

The quantities of each ingredient may be varied from the above for other drugs to obtain optimum formulations and therapeutic efficacy. The above formulations are designed to be accommodated into a hard or a soft gelatin capsule.

Where the above formulations are encapsulated within soft gelatin capsules the shell comprises.

| Gelatin | 57.65% w/w |
|---|---|
| Glycerin | 28.95% w/w |
| Silicone Oil | 13.14% w/w |
| Potassium Sorbate(preservative) | 0.26% w/w |

EXAMPLES 4-6

Three oil based formulations containing the peptide drugs insulin, calcitonin and human growth hormone respectively, for encapsulation in capsules embodying the invention are as follows.

| Ingredient | Example 4 Insulin | Example 5 Calcitonin (Pork) | Example 6 Human Growth Hormone |
|---|---|---|---|
| Peptide | 20 i.u. (ca. 1 mg) | 80 i.u. (ca. 1 mg) | 4 i.u. (ca. 2 mg) |
| Sodium 5-methoxy salicylate (1) | 150.0 mg | 150.0 mg | 150.0 mg |
| Fat Mix (5) | 15.0 mg | 15.0 mg | 15.0 mg |
| Soya lecithin (2) | 3.0 mg | 3.0 mg | 3.0 mg |
| Tween TM 80 (3) | 7.5 mg | 7.5 mg | 7.5 mg |
| Miglyol TM 812 (4) | 123.5 mg | 123.5 mg | 122.5 mg |
| Capsule fill wt. | 300.0 mg | 300.0 mg | 300.0 mg |

(1) absorption promoter
(2) wetting agent
(3) a 20-mole oxyethylated sorbitan monooeate surfactant
(4) A triglyceride of a fractionated coconut oil $C_{8-10}$ fatty acids (mainly caprylic and capric), as suspension medium
(5) thickener The above formulations are encapsulated within hard gelatin capsules, or within soft gelatin capsules of the shell formulation given for Examples 1-3.

EXAMPLES 7-9

Three oil based formulations similar to those of Examples 4-6 but containing larger concentrations of surfactant are as follows.

| Ingredient | Example 7 Insulin | Example 8 Calcitonin (Pork) | Example 9 Human Growth Hormone |
|---|---|---|---|
| Peptide | 20 i.u. (ca. 1 mg) | 80 i.u. (ca. 1 mg) | 4 i.u. (ca. 2 mg) |
| Sodium 5-methoxy salicylate | 150.0 mg | 150.0 mg | 150.0 mg |
| Fat Mix | 15.0 mg | 15.0 mg | 15.0 mg |
| Soya lecithin | 3.0 mg | 3.0 mg | 3.0 mg |
| Tween 80 | 45.0 mg | 45.0 mg | 45.0 mg |
| Miglyol 812 | 86.0 mg | 86.0 mg | 85.0 mg |
| Capsule fill wt. | 300.0 mg | 300.0 mg | 300.0 mg |

The above formulations of Examples 7-9 are designed to be accommodated into soft or hard gelatin capsules, for example, soft gelatin capsules of the shell formulation given in Examples 1-3. Formulations containing high surfactant concentrations (Examples 7-9) may promote self-emulsification of the capsule contents in an aqueous medium. Furthermore at such high concentrations, the surfactant will additionally assist in absorption promotion.

In each formulation type, the quantities of each ingredient may be varied for a given drug to obtain optimum formulations and therapeutic efficacy. The choice of a surfactant is not restricted to Tween 80; other surfactants satisfying regulatory and performance requirements may alternatively be employed.

Examples of capsules embodying the invention

The drugs and additives used for the dosage form formulations were: porcine insulin Leo Neutral 100 iu ml$^{-1}$ (Nordisk Gentofte, Denmark) and $^{125}$I porcine insulin (NEN) with a specific activity of 99μCi μg$^{-1}$ and a radiochemical purity of 98%. Sodium laurate and cetyl alcohol (Sigma) were "chemically pure" substances and arachis oil conformed to the B.P. requirements.

Dosage Form Design:

The oral dosage form design was based on the incorporation of an insulin formulation into soft gelatin capsules coated with polyacrylic polymer -Eudragit (TM) (Rohm Pharma, Germany) - having pH-dependent solubility properties. The soft capsules were filled with various compositions according to their use during the experiment. The compositions are presented in Table 1. Organic solvent solutions of Eudragit RS, L and S at various ratios were used to coat the capsules (Table 2).

Preparation of the Formulation (Table 1)

800 ml of porcine insulin solution (Leo Neutral) was mixed with 40 mg sodium laurate and 160 mg cetyl alcohol (small pieces) and was heated to 40° C. The arachis oil was added to obtain 1000 mg preparations. Soft gelatin capsules containing arachis oil were emptied using a syringe and filled with the active preparation. The whole was closed with melted gelatin.

In Vitro Insulin Release Measurements:

The coating effectiveness was tested in vitro using the USP disintegration apparatus USP XIX, 1975. The release media used were artificial gastric juice (60 ml N HCl per liter and buffer phosphate solutions of respective pH's 6.0, 6.5, 7.0, 7.5, and 8.0. In each experiment six capsules were tested for 1 hour in gastric juice, briefly rinsed with distilled water and transferred to a phosphate buffer solution.

The in vitro pH-dependent release course was tested by scintillation counting using $^{125}I$ insulin diluted with cold insulin (Table 1), the USP dissolution basket and 400 ml phosphate buffer solution. Each value given is the mean of 3 experiments.

Animal Experimental Design:

Results obtained by direction of insulin into selected regions of the gastro-intestinal lumen suggested that it would be worthwhile to investigate the effectiveness of oral dosage forms designed to deliver insulin in the presence of an absorption promoter in that part of the intestine where the proteolysis is relatively low.

The rationale of choosing gelatin capsules as dosage forms is based on the wide formulation possibilities offered by this form: (1) incorporation of oily compositions in which insulin and promoter are molecularly dispersed, (2) coating for targeting the drug release into the colon.

Hebrew University strain male rats (270 g) were starved for 20 hours before the experiment. During the experiment the rats received water ad libitum. The capsules were administered to the rats according to the study design presented in Scheme 1. The absorption of the intact insulin was evaluated by measuring the hypoglycemia effect. Blood was collected from the rats' tails immediately before capsule administration and at ½, 1, 2, 3, 4 and 6 hours afterwards. The rats were etheranaesthetized during blood collection. Blood glucose concentrations were determined at 610 nm using the GOD-Perid method (Boehringer, Germany).

The formulations presented herein were selected from a number of compositions screened for the effects of: chain length ($C_{10}$-$C_{16}$) of the anionic surfactant used as absorption promoter, composition of the mixed emulsifiers and viscosity. The capsules were coated with mixtures of various ratios of Eudragit RS, S and L (Table 2) and tested for disintegration and insulin release properties by the procedures described above. Some of the relevant release profiles are presented in FIGS. 1 and 2.

The selected capsules were administered to rats following the protocol presented in Scheme 1, and the results were compared with those obtained by intraperitoneal administration of 4 iu neutral insulin.

Figure 3:
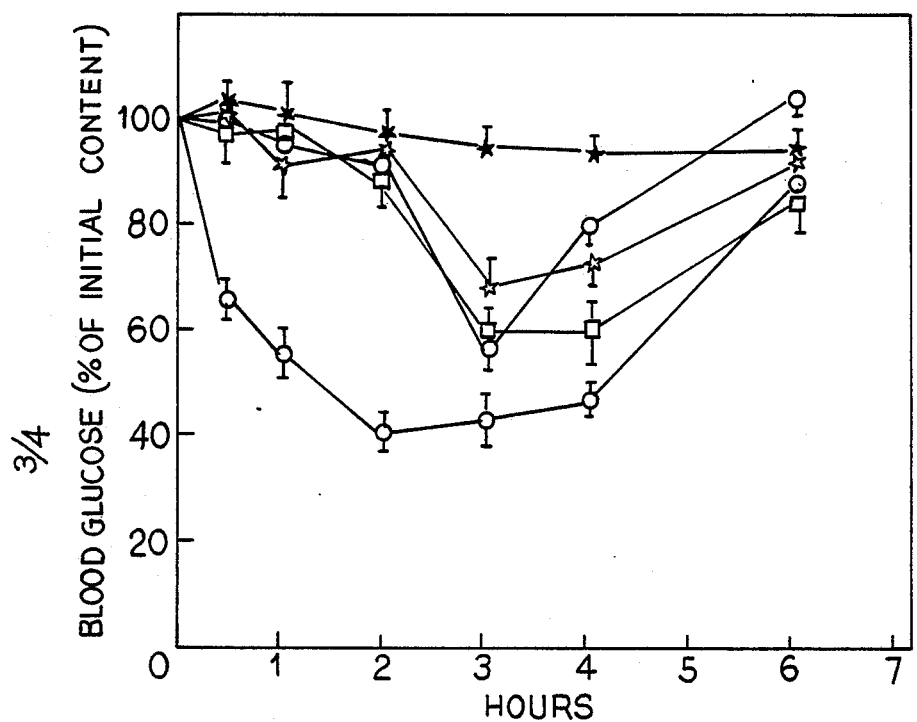

The mean of the blood glucose concentration of the samples prior to dosage administration was used as a baseline for plotting the response versus time curves. FIG. 3 presents the changes in blood glucose concentration that occurred after oral and intraperitoneal treatment. It is interesting to note the lag time of two hours that occurred for each insulin oral regime tested. The effect of RS2 is higher (45% reduction in glycemia) but shorter (it lasted for about one hour) than RS1.

It was suggested that one of the causes of the short duration of enteral administration of insulin with promoter may reside in a difference in the absorption rate, from the intestinal tract, of insulin and promoter. To test this hypothesis, capsules containing only the surfactant were administered, in one trial before and in one trial after insulin administration. No change was observed by pre-treatment. However, the surfactant given 30 minutes post-insulin oral treatment extended the duration of RS2 by about one hour, improving the drug bioavailability. Similar results have been obtained by Nishihata et al, J. Pharm, Pharmacol. (1985), 37, 22-26, who reported that post-administration of promoter (enamine) in rectal dosage of insulin in dogs improved the bioavailability from 19.4% to 38.2%.

Curves of % glucose and % glucose reduction versus time were plotted (see FIGS. 3 and 4) and the area under the % glucose reduction versus time curve (AUC), the maximum glucose reduction ($C_{max}$) and the time of the maximum effect ($t_{max}$) were estimated from these curves. Their values are given in Table 3. A schematic comparison of the AUC of orally administered insulin (RS2) and intraperitoneally administered insulin clearly indicates that the oral preparation is effective, but its bioavailability is relatively low. The $C_{max}$ obtained with formulation RS2 (p 0.01) and the prolongation effect of post-administration of promoter are worth noting.

TABLE 1

| Materials | Composition for soft gelatin capsues | | |
|---|---|---|---|
| | Caps. Ins. 1* | Caps. Ins. 2** | Caps Surf** |
| Porcine insulin | 8 iu | 8 iu | — |
| $^{125}$I insulin (porcine) | 5 μCi | — | — |
| Sodium laurate | 4 mg | 4 mg | 4 mg |
| Cetyl alcohol | 16 mg | 16 mg | 16 mg |
| Arachis oil to | 100 mg | 100 mg | 100 mg |

*tested in vitro
**administered in vivo
Caps. Ins. 1 - capsules containing labelled isulin, insulin diluent and surfactant
Caps. Ins. 2 - capsules containing insulin, diluent and surfactant
Caps. Surf. - capsules containing no insulin but containing surfactant.

Scheme 1

| Scheme 1 No. of rats | No. of caps adminstered per rat | | |
|---|---|---|---|
| | Caps. Ins. (RS1) | Caps. Ins. (RS2) | Caps. Surf. (RS2) |
| 5 | 2 | — | — |
| 5 | — | 2 | — |
| 5 | — | 2 | 1* |
| 5 | — | 2 | 1** |
| 4 | — | — | 2 |

Given 30 minutes *after **before insulin capsules' administration.

The above insulin capsules all contain the formulation referred to as Caps. Ins.2 in Table 1, which includes surfactant.

TABLE 2

The Eudragit RS, S and L ratios used for coating the capsules*

| Formulation | Eudragit | | |
|---|---|---|---|
| | RS | S | L |
| RS | 2 | — | 8 |
| RS1 | 4 | 6 | — |
| RS2 | 2 | 2 | 6 |
| RS3 | 1 | — | 9 |
| LS | — | 7 | 3 |

*solvents: acetone and isopropyl alcohol

TABLE 3

Some pharmacokinetic parameters related to the hypoglycemia effect in rats of insulin upon oral administration of soft capsules coated with Eudagit compared with intraperitoneal administration.

| Treatment | Loading dose iu | Dose iu kg$^{-1}$ | AUC | $C_{max}$ % glucose reduction | $t_{max}$ hr. |
|---|---|---|---|---|---|
| i.p. | 4 | 15 | 258 | 58 | 2 |
| p.o. RS1 | 16 | 59 | 110 | 45 | 3 |
| RS2 | 16 | 59 | 96 | 32 | 3 |
| RS2 + Surf | 16 | 59 | 131 | 42 | 3 | i.p. intra-peritoneal
p.o. oral

LEGEND

Figure 1:
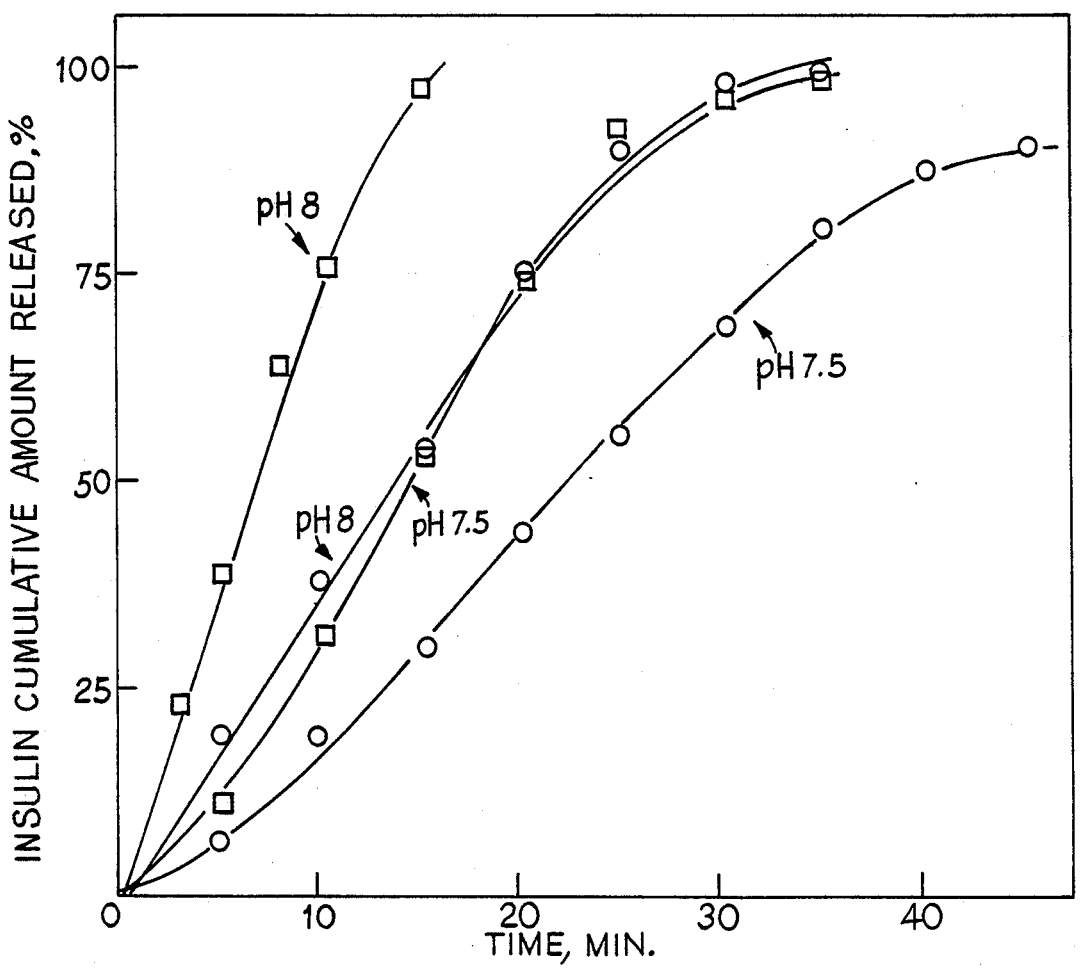
FIG. 1 shows the time release cource at pH's 7.5 and 8.0 of two formulations, RS1 and RS2, selected to be orally administered to rats. The drug percent released was estimated from the $^{125}I$ insulin counted by scintillation. It can be observed that the time required for 95% of the drug to be released is relatively short, 15 to 40 minutes, and depends on coating and pH. Although for both formulations the time is shorter at pH 8.0 than at pH 7.5, the rate of release from RS1 is much slower than from RS2; thus, the percent released in the first fifteen minutes was 95% versus 53% for RS2 and RS1, respectively. A lag time of two minutes could be detected at pH 8.0; whereas at pH 7.5, the release process was instantaneous. These release properties of RS1 and RS2 are convenient for the colon content milieu. Moreover, their choice was based on the release behaviour in a wide pH range (6 to 8) as presented in FIG. 2. The pH-dependent release courses indicate that formulations RS1 and RS2 do not release detectable amounts of insulin at a pH lower than pH 7. The other formulations tested, RS, RS3 and LS, release considerable amounts of drug at pH 6.5 and pH 7.0 corresponding to upper-intestinal regions. These formulations were considered unsuitable for our purpose even though their release rates at pH's 7.5 and 8.0 were higher than that of the chosen formulations RS1 and RS2 (FIG. 2).
Figure 2:
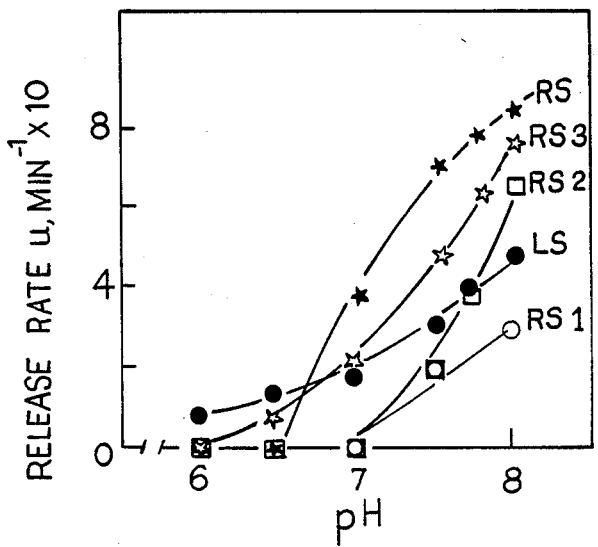

FIG. 1; Release profiles of insulin from capsules coated with Eudragit mixtures tested at pH 7.5 and pH 8. Formulations: ○ RSI; □ RS2, FIG. 2; Effect of pH on the release rate of insulin from soft capsules coated with various mixtures of Eudragit S, L and RS (see description of FIG. 3 below).

FIG. 3; Hypoglycemic effect of insulin administered orally to normal rats by means of coated soft capsules containing an absorption enhancing formulation (for formulation see Table 1). Symbols for FIGS. 2 and 3: ☆2 capsules RS1, ○2 capsules RS2, □2 capsules RS2+1 capsules surfactant post-insulin administration, ●insulin i.p. 4 iu, ★2 capsules surfactant (no insulin). Each point is the mean ± SD of 5 animals for insulin administration and of 4 animals for controls.

Figure 4:
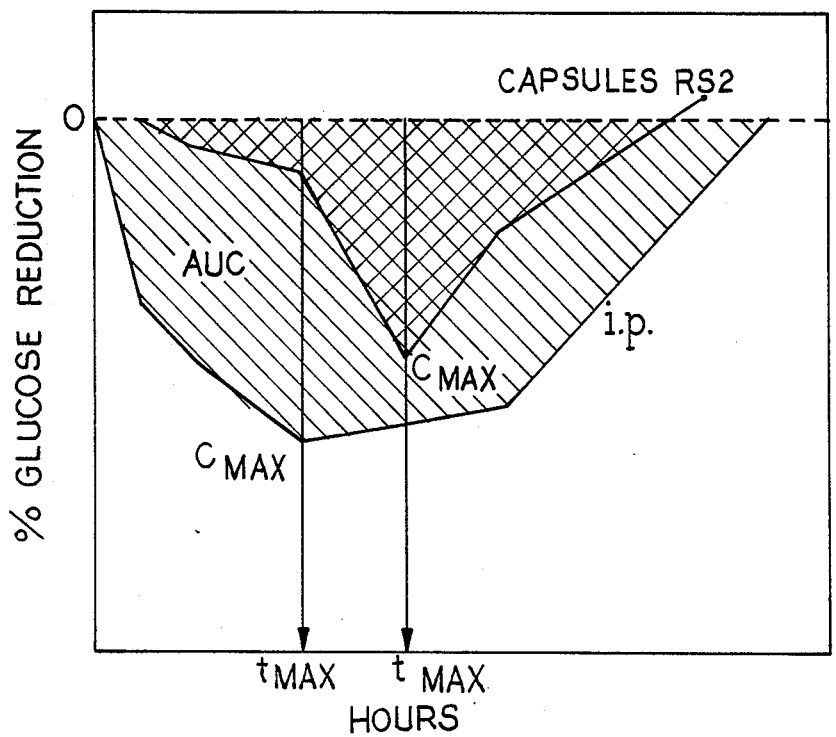

FIG. 4; Area under the curve (AUC) of the % blood glucose reduction versus time (hr.) profile upon oral administration of 16 iu insulin in coated capsules as compared with intraperitoneal administration of 4 iu insulin.

The use of a coating, such as a Eudragit coating, especially a Eudragit RS1 or RS2 coating as described above on a gelatin capsule with a pharmaceutical composition containing an absorption promoter within the capsule provides an excellent delivery system enabling oral administration of a drug which until now could only be administered by injection.

We claim:

1. An orally administered enteric coated capsule for colonic absorption of a pharmaceutical composition contained therein comprising a capsule shell, an enteric coating, and a pharmaceutical composition;

said capsule shell being of either hard or soft and of the carbohydrate or gelatin type, containing said enteric coating thereon, and said pharmaceutical composition therein;

said enteric coating comprising a film forming composition that is sufficiently insoluble at a pH below 7 as to be capable of protection said capsule and said pharmaceutical composition contained therein from digestive juices below said pH 7, said film forming composition being sufficiently soluble at a pH above 7 as to be capable of permitting the erosion or dissolution of said capsule and the release of said pharmaceutical composition contained therein;

said pharmaceutical composition comprising an active ingredient and an absorption promoter, said active ingredient being a peptide or protein that is unsuited for absorption by any portion of a gastrointestinal tract wherein the pH is below 7, said absorption promoter enhancing absorption of said active ingredient in the colon and being selected from the group consisting of organic aromatic acids, their esters, amides and pharmaceutically acceptable salts thereof:

such that when said enteric coated capsule is orally administered, said capsule passes intact through the stomach and into the intestinal tract where it continues to pass intact until it encounters an environment having a pH above 7 in the distal intestine and/or colon, said environment eroding and/or dissolving said enteric coating thereby permitting the erosion and/or dissolution of said capsule shell thereunder and the release of said pharmaceutical composition contained within said capsule, whereupon a pharmaceutically effective amount of said active ingredient is colonically absorbed from said environment.

2. A capsule according to claim 1, wherein the active ingredient is a protein.

3. A capsule according to claim 2, wherein said protein is insulin or a pharmaceutically active fragment thereof.

4. A capsule according to claim 1, wherein the said peptide or protein is selected from the group consisting of gastrin, pentagastrin, calcitonin, human growth hormone, glucagon, adrenocorticotrophic hormone, leutinising releasing hormone, enkephalin, oxycotin, parathyroid hormone, thyrotropic releasing hormone and vasopressin.

5. A capsule according to claim 1, wherein said aromatic carboxylic acid or said salt thereof is salicylic acid, a substituted salicylic acid or a pharmaceutically acceptable salt thereof.

6. A capsule according to claim 5, wherein said substituted salicylic acid is a member of the group consisting of 5-methoxysalicylic acid; 5-methylsalicylic acid; 3-methylsalicylic acid; 5-tert-octylsalicylic acid; 3-tert-butyl-6methylsalicylic acid; 3,5-diisopropylsalicylic acid; 3-tert-butyl-5-methylsalicylic acid; 5-bromosalicylic acid; 3,5-diiodosalicylic acid; 3-methoxysalicylic acid; 5-octyloxysalicylic acid; 5-butoxysalicylic acid; and 5chlorosalicylic acid; and said pharmaceutically acceptable salt thereof is a sodium salt of any of the said acids.

7. A capsule according to claim 1, wherein the absorption promoter is selected from the group consisting of homovanillic acid; 2,5-dihydroxy-benzoic acid; 2,4-dihydroxybenzoic acid; 5-methoxy-2-hydroxy-phenylsulfonic acid; guaicolsulfonic acid; 2-hydroxyphenylacetic acid; 2-hydroxyphenyl-methanesulfonic acid; 5-trifluoromethyl-2-hydroxybenzoic acid; 2-hydroxy-3-methoxy-benzoic acid; and the sodium salt of any of the said acids.

8. A capsule according to claim 2, wherein the absorption promoter is selected from the group consisting of 5-methoxysalicylic acid; salicylic acid; 2,5-dihydroxybenzoic acid; 2,4-dihydroxybenzoic acid; 3-methylsalicylic acid; 5-methylsalicylic acid; 5-tert-octylsalicylic acid; 3-tert-butyl-6-methylsalicylic acid; 3,5-diisopropylsalicylic acid; 3-tert-butyl-5-methylsalicylic acid; 5-bromosalicylic acid; 3,5-dibromosalicylic acid; 5-iodosalicylic acid; 3,5-diiodosalicylic acid; 2-hydroxyphenylacetic acid; 5-trifluoromethyl-2-hydroxybenzoic acid; 3-methoxysalicylic acid; 5-octyloxysalicylic acid; 5-butoxysalicylic acid; 5-chlorosalicylic acid; 2-hydroxy-3-methoxybenzoic acid; and the sodium salt of any of the said acids 9. A capsule according to claim 1, wherein said capsule shell comprises a gelatin composition.

10. A capsule according to claim 1, wherein the film forming composition comprises a mixture of anionic acrylic copolymers derived from at least one monomer selected from acrylic and methacrylic acids and methyl acrylates.

11. A capsule according to claim 10, wherein the mixture of acrylic copolymers comprises a first said copolymer being derived from acrylic and methacrylic acid esters with a low content of quaternary ammonium groups, the molar ratio of the said quaternary ammonium groups: the said ester groups being about 1:40, and having a mean molecular weight of about 150,000, and a second said copolymer being derived from methacrylic acid and methyl methacrylate, the molar ratio of free carboxyl:ester groups being about 1:2, and having a mean molecular weight of about 135,000, the said first and second copolymers being present in the mixture in a proportional amount of 2:3 respectively.

12. A capsule according to claim 10, wherein the mixture of acrylic copolymers comprises a first said copolymer being derived from acrylic and methacrylic acid esters with a low content of quaternary ammonium groups, the molar ratio of the said quaternary ammonium groups: the said ester groups being about 1:40, and having a mean weight of about 150,000, a second said copolymer being derived from methacrylic acid and methyl methacrylate, the molar ratio of free carboxyl:ester groups being about 1:2, and having a mean molecular weight of about 135,000, and a third said copolymer being derived from methacrylic acid and methyl methacrylate, the molar ratio of free carboxyl:ester groups being about 1:1 and having a mean molecular weight of about 135,000, the said first, second and third copolymers being present in the mixture in a proportional amount of 1:1:3 respectively.

* * * * *

UNITED STATES PATENT AND TRADEMARK OFFICE
CERTIFICATE OF CORRECTION

PATENT NO. : 4,910,021

DATED : March 20, 1990

INVENTOR(S) : John D. Davies, Elka Touitou, Ardon Rubinstein

It is certified that error appears in the above-identified patent and that said Letters Patent is hereby corrected as shown below:

ON TITLE PAGE:

In the banner on the first page of the patent, the name "Davis et al." should be changed to "Davies et al."

In the list of inventors, the surname of the first-listed inventor should be changed from "Davis" to "Davies".

In the title of the patent, the word "Enternal" should be changed to "Enteral".

In the heading on the first line in the first page of text to the patent, the word "Enternal" should be changed to "Enteral".

Signed and Sealed this

Fourteenth Day of January, 1992

Attest:

HARRY F. MANBECK, JR.

*Attesting Officer*     *Commissioner of Patents and Trademarks*